US009044275B2

(12) United States Patent
Weiman et al.

(10) Patent No.: US 9,044,275 B2
(45) Date of Patent: Jun. 2, 2015

(54) CERVICAL SPINE STABILIZATION SYSTEM WITH EXTENDABLE PLATES

(75) Inventors: Mark Weiman, Coatesville, PA (US); Frank Guntz, Telford, PA (US); Lawrence Binder, Croydon, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 949 days.

(21) Appl. No.: 12/275,348

(22) Filed: Nov. 21, 2008
(Under 37 CFR 1.47)

(65) Prior Publication Data
US 2009/0163960 A1    Jun. 25, 2009

Related U.S. Application Data

(60) Provisional application No. 60/989,622, filed on Nov. 21, 2007.

(51) Int. Cl.
*A61B 17/70* (2006.01)
*A61B 17/80* (2006.01)
*A61B 17/17* (2006.01)

(52) U.S. Cl.
CPC ......... *A61B 17/7059* (2013.01); *A61B 17/1728* (2013.01); *A61B 17/8023* (2013.01); *A61B 17/8033* (2013.01); *A61B 17/808* (2013.01); *A61B 17/1757* (2013.01)

(58) Field of Classification Search
CPC ................................................ A61B 17/8004
USPC ................... 606/71, 279, 280, 282, 283, 286
See application file for complete search history.

(56) References Cited

U.S. PATENT DOCUMENTS

| | | | |
|---|---|---|---|
| 6,666,867 B2 | 12/2003 | Ralph | |
| 6,689,134 B2 | 2/2004 | Ralph | |
| 6,699,249 B2 | 3/2004 | Schlapfer | |
| 6,761,721 B2 | 7/2004 | Burgess | |
| 6,786,907 B2 | 9/2004 | Lange | |
| 6,852,113 B2 | 2/2005 | Nathanson | |
| 6,926,718 B1 | 8/2005 | Michelson | |
| 6,932,820 B2 | 8/2005 | Osman | |
| 7,033,377 B2 | 4/2006 | Miller, III | |
| 7,399,301 B2 | 7/2008 | Michelson | |
| 7,635,364 B2 | 12/2009 | Barrall | |
| 2002/0045896 A1* | 4/2002 | Michelson | ...... 606/61 |
| 2004/0092939 A1 | 5/2004 | Freid et al. | |
| 2004/0167521 A1 | 8/2004 | De Windt | |
| 2004/0181226 A1* | 9/2004 | Michelson | ...... 606/61 |
| 2005/0004573 A1 | 1/2005 | Abdou | |
| 2005/0010227 A1 | 1/2005 | Paul | |
| 2005/0107795 A1 | 5/2005 | Morris | |

(Continued)

FOREIGN PATENT DOCUMENTS

DE    202007001585 U1    6/2007

*Primary Examiner* — Christian Sevilla

(57) ABSTRACT

A spine stabilization system having a base plate having a plurality of screw holes and a plurality of corresponding screw locking mechanisms. The present invention also provides an extension plate having a plurality of screw holes and corresponding screw locking mechanisms. The extension plate is dimensioned and configured with an extension portion, the extension portion having a screw hole and a screw locking mechanism and a finger portion having a connection element and to couple with the base plate. The base plate is provided a graft window having edges, wherein at least one of the edges being configured to receive and connect with the connection element.

19 Claims, 16 Drawing Sheets

(56) References Cited

U.S. PATENT DOCUMENTS

| | | |
|---|---|---|
| 2005/0137597 A1 | 6/2005 | Butler et al. |
| 2006/0116681 A1 * | 6/2006 | Bert ................................ 606/69 |
| 2006/0217724 A1 | 9/2006 | Suh et al. |
| 2006/0229619 A1 | 10/2006 | Orbay et al. |
| 2006/0276794 A1 | 12/2006 | Stern |
| 2010/0121328 A1 | 5/2010 | Reitzig et al. |

* cited by examiner

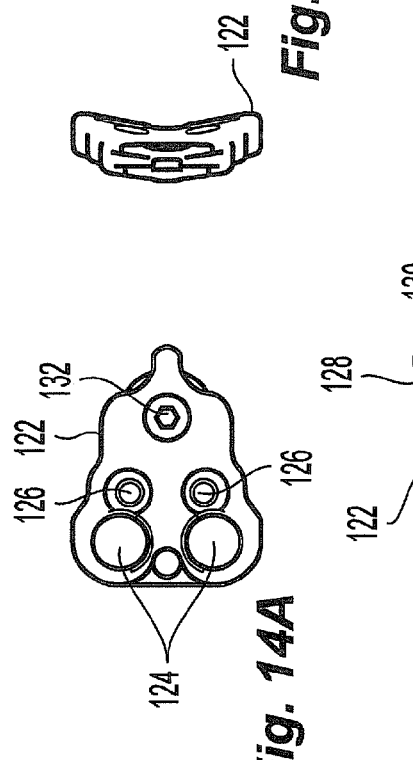
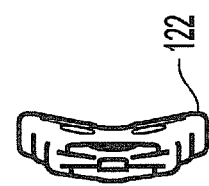
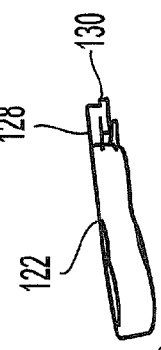
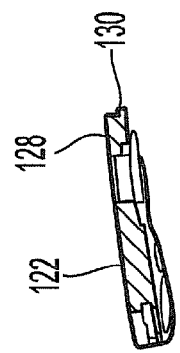
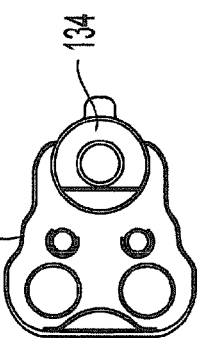
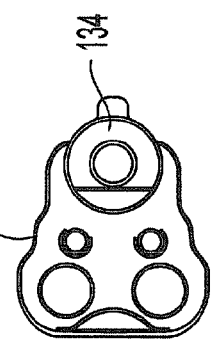
Fig. 14A
Fig. 14B
Fig. 14C
Fig. 14D
Fig. 14E
Fig. 15A
Fig. 15B
Fig. 15C
Fig. 15D
Fig. 15E

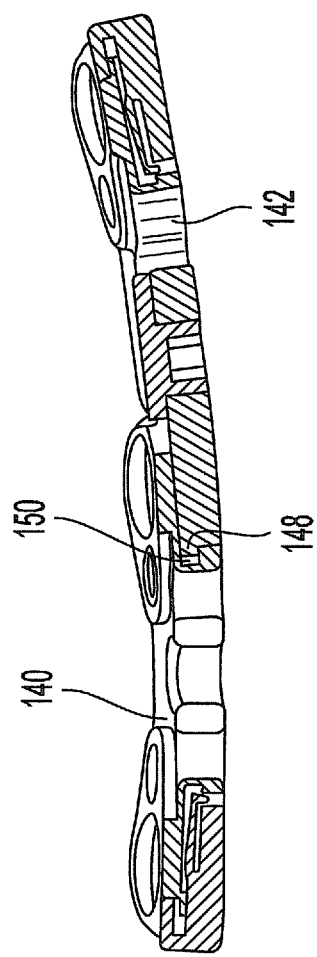

CERVICAL SPINE STABILIZATION SYSTEM WITH EXTENDABLE PLATES

CROSS-REFERENCE TO RELATED APPLICATIONS

This application claims the benefit of U.S. Provisional Application No. 60/989,622 filed on Nov. 21, 2007.

FIELD OF THE INVENTION

The present invention is generally directed for use in a cervical spine stabilization system. In particular, the present invention is directed to a cervical spine stabilization system for the anterior cervical region of the human spine that specifically addresses an adjacent level condition and provides additional segments for the cervical spine stabilization system.

BACKGROUND OF THE INVENTION

In the United States, millions are affected by neck pain. Most patients respond well to non-surgical treatments. However, many others are required to find other solutions to alleviate the pain. If the neck pain persists and in addition, other symptoms such as arm pain and neurological dysfunction occur, the cause may be a cervical intervertebral disc that has herniated. A disc herniates when some of the disc's gel like center bulges or ruptures through the outer ring of the disc and presses on nerve roots or the spinal cord. Surgery is an option for those suffering from this type of nerve compression. To alleviate the pain, a surgeon may perform a procedure called an anterior cervical discectomy and fusion. In this procedure, the surgeon makes a small incision in the front of the neck to reach the cervical spine. The disc is removed and the space is filled with a bone graft. A cervical plate is then screwed into the superior and inferior vertebral bones, which stabilizes the cervical spine facilitating fusion and healing.

However, a second surgery may be required to repair bone injuries to adjacent bone segments. Adjacent segment disease is a documented problem within the human cervical spine. As a result, surgeons currently remove the plate that was used to the fuse the original segment and position a new plate in its position. Other solutions to overcome this problem have been used. In one instance, the original plate is lifted up at one end and a larger second plate is positioned underneath the original plate and tightened down, thereby compressing and stabilizing the original plate and the new larger plate. However, the procedural requirement along with the size and connection method for this solution have created additional problems. Thus, the present art does not provide a novel system for additional plates to be attached to the base plate with ease, i.e. minimal incision during surgery. Therefore, there is a need for a cervical plating system having the ability to incorporate additional plates that can be attached to the base plate with minimal surgery time and alleviate the problems associated with adjacent segment disease.

SUMMARY OF THE INVENTION

The present invention provides an anterior spine stabilization system having a base plate that has a plurality of screw holes and a plurality of corresponding screw locking mechanisms and an extension plate having a plurality of screw holes and corresponding screw locking mechanisms. The extension plate is dimensioned and configured with an extension portion, and the extension portion is provided with an angled screw hole and a screw locking mechanism. The extension portion is also provided with a finger portion having a connection element to contact and connect with the base plate. The base plate is provided with graft windows having edges and at least one of the edges being configured to receive and connect with the connection element.

BRIEF DESCRIPTION OF THE DRAWINGS

The attached figures illustrate the different embodiments of the present invention.

FIGS. 14A-14E are the top, bottom and side views of the adjacent segment plate according another embodiment of the present invention;

FIGS. 15A-15E are the top, bottom and side views of the fastening element according one embodiment of the present invention;

FIGS. 17A-17C are the top, bottom and side view of the plating system according to the embodiment illustrated in FIG. 16;

DETAILED DESCRIPTION OF THE INVENTION

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected.

It is to be understood that each specific element includes all technical equivalents that operate in a similar manner to accomplish a similar purpose.

While the invention herein disclosed has been described by means of specific embodiments and applications thereof, numerous modifications and variations can be made thereto by those skilled in the art without departing from the scope of the invention.

The present invention includes a base plate provided with features formed within the geometry of the plate to allow for joining of the extension plates. These additional plates can be later added in both the superior and the inferior directions.

The primary, initially implanted plate is placed in the appropriate location on the patient spine. Plates of this type are usually implanted in patients that must undergo an anterior cervical discectomy and fusion. After the graft has fused with healthy bone growth, some patients may develop conditions to adjacent vertebra warranting further fusion and surgery to repair these conditions. An extension plate may be implanted so that the previous repair involving the implementation of a primary or base plate does not have to be removed.

Since surgeons request that the adjacent segment plate is implanted in a minimally invasive manner, the present invention provides a plate system that allows the incision to be as small as possible to orient, maneuver and implant the device into the patient. The attached drawings illustrate the elements of the present invention. Design and utility features of the present invention are also disclosed. It should be noted that the angle of the attachment plates can be designed to be different shapes that correspond to the locking mechanisms.

FIGS. 1-4 illustrate a plate system 10 according to one embodiment of the present invention. The plate system 10 consists of base plate 12 and an extension plate 14 used with variable or fixed angle screws. The base plate 12 is used in the initial procedure and attaches to the anterior portion of the vertebral body of the cervical spine.

In the event that a secondary procedure is required to address conditions arising in the adjacent spinal segments to the pre-treated spinal segments, the extension plate 14 can be used to treat adjacent segment disease and provide an option to attach onto the cephalad or caudal end of the base plate without the removal of the base plate. The present invention enables a surgeon to incorporate an extension plate rather than removing an original base plate and implanting a new base plate.

Figure 1:
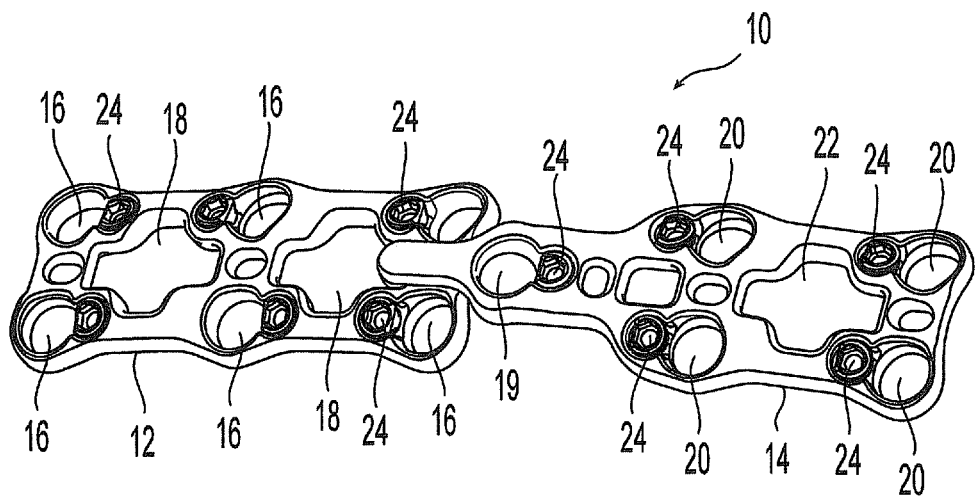
FIG. 1 is an isometric view of one particular embodiment of the present invention.
Figure 2:
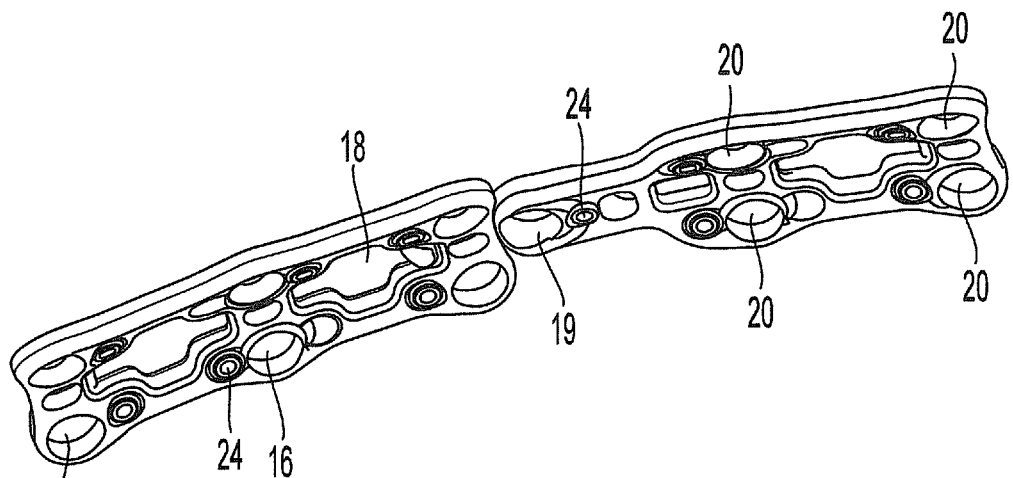
FIG. 2 is a top view of the present invention illustrated in FIG. 1.

As illustrated in FIG. 1, the cervical plate system 10 includes a base plate 12, and an extension plate 14. The base plate 10 includes a plurality of screw holes 16 and graft windows 18. The extension plate 14 is also provided with screw holes 20 and graft windows 22. As illustrated in FIGS. 1-4, the base plate 12 and the extension plate 14 are configured and dimensioned to be connected to each other via a finger element associated with the extension plate 14. Both the base plate 12 and the extension plate 14 are provided in a variety of sizes to accommodate surgical needs and anatomic requirements. The base plate 12 and the extension plates 14 are configured and dimensioned to accommodate between 1 and 5 levels of the cervical spine.

Lengths are measured from cephalad to caudal screw hole distance (i.e. hole-to-hole distance). The base plates generally have the following lengths:

| Base Plates | |
| --- | --- |
| 1 Level: | 10, 12, 14, 16, 18, 20, 22, 24, 26 mm |
| 1 Level Extra Lordotic: | 10, 12, 14, 16 mm |
| 2 Level: | 24, 26, 28, 30, 32, 34, 36, 38, 40, 42, 44, 46 mm |

| Base Plates | |
| --- | --- |
| 2 Level Extra Lordotic: | 26, 28 mm |
| 3 Level: | 39, 42, 45, 48, 51, 54, 57, 60, 63, 66, 69 mm |
| 4 Level: | 60, 63, 66, 69, 72, 75, 78, 81, 84, 87, 90, 93 mm |
| 5 Level: | 80, 83, 86, 89, 92, 95, 98, 101, 104 mm |

| Extension Plates | |
| --- | --- |
| 1 Level: | 10, 12, 14, 16, 18, 20, 22, 24, 26 mm |
| 1 Level Extra Lordotic: | 10, 12, 14, 16 mm |
| 2 Level: | 24, 26, 28, 30, 32, 34, 36, 38, 40, 42, 44, 46 mm |
| 2 Level Extra Lordotic: | 26, 28 mm |

The base plate 12 and the extension plates 14 are connected to the vertebrae through bone screws, which are positioned in the screw holes 16, 20. The bone screws may be comprised of any material, such as a metal, alloy, or any combination of the two. The material used to construct the plate and the screws allows the plate to maintain its structural integrity while allowing for a desired amount of resiliency. Furthermore, the material used is preferably biocompatible and capable of withstanding the conditions of a body over a desired period of time. In some embodiments, this is achieved by manufacturing the plate and screws using metals such as titanium or stainless steel. Titanium has sufficient ductility to permit a desired amount of curving of the plate to conform to the shape of the vertebrae, yet has the strength to maintain its structural integrity.

The base plate 12 of the present invention is intended to be positioned with its longitudinal axis collinear with the spinal midline, and to be mounted on the anterior surface of the vertebral bodies. The length of the plate as well as the number of screw holes in the plate will vary depending upon the number of vertebral bodies to be fused.

Figure 3:
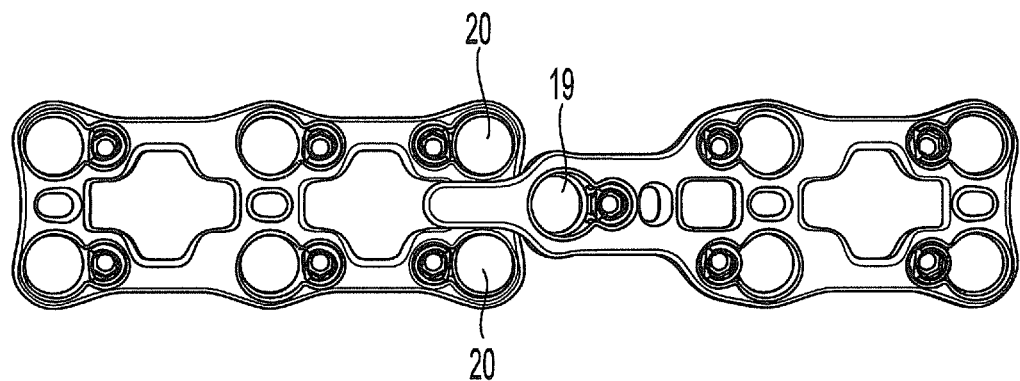
FIG. 3 is a top view of the present invention according the embodiment illustrated in FIG. 1.
Figure 4:
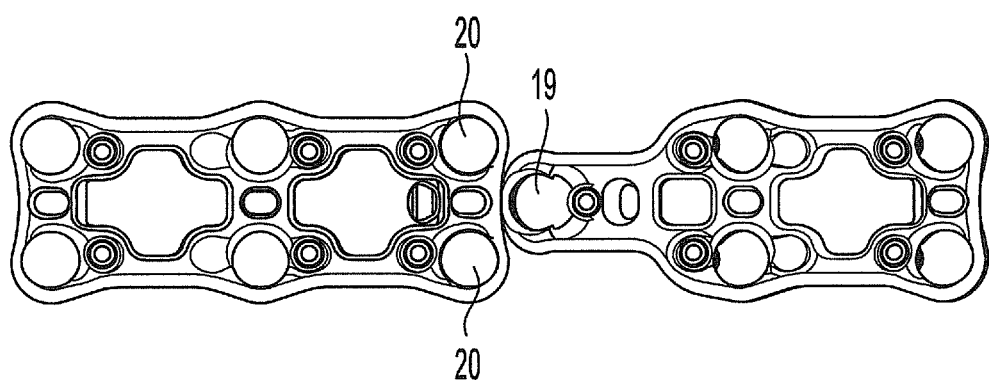
FIG. 4 is a bottom view of the present invention according to the embodiment illustrated in FIG. 1.

FIGS. 3 and 4 illustrate the top and bottom view of the plating system according the present invention. FIG. 4 clearly illustrates the screw hole 19 according to the present invention. The screw hole 19 is capable of receiving bone screws, which are directed to be inserted within the vertebra while stabilizing and coupling the extension plate to the vertebrae. In this embodiment of the present invention, the screw hole 19 is configured so that the bone screw, when inserted, is directed at an angle in which the bone screw is situated between the bone screws that have already been inserted through screw holes 20 and into the vertebrae for implanting the base plate. The base plate 12 and the extension plate 14 each will be discussed in greater detail with reference to FIGS. 5, 6, 7, and 8.

Figure 5:
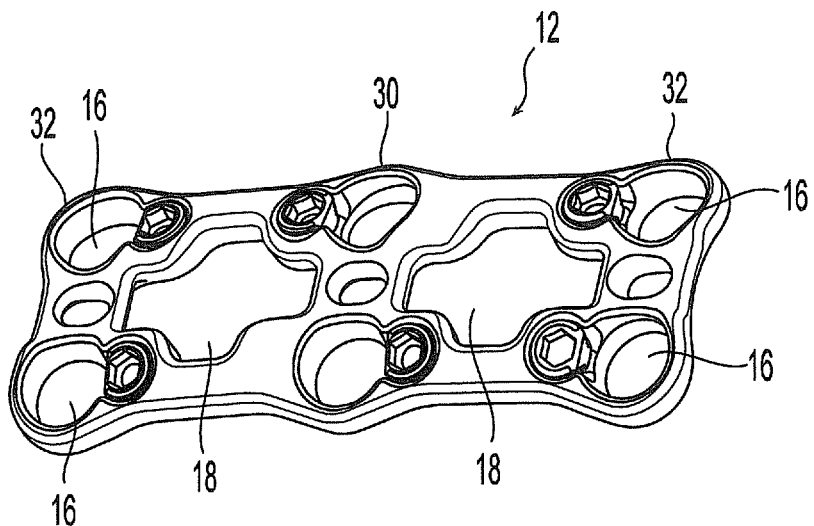
FIG. 5 is an isometric view of the base plate according to the present invention.
Figure 6:
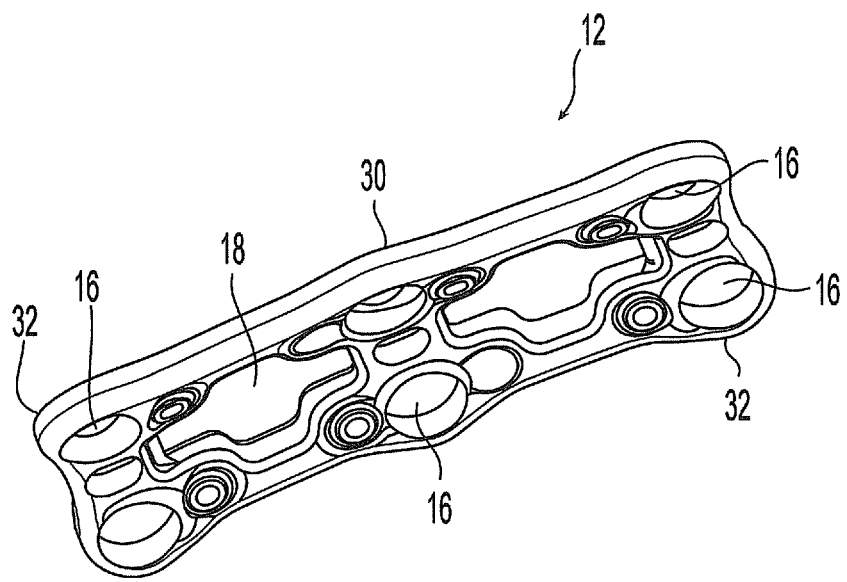
FIG. 6 is a bottom view of the base plate shown in FIG. 5.

FIGS. 5 and 6 illustrate a top view and a bottom view of the base plate 12. In this particular embodiment, the base plate 12 comprises of a center portion 30 and two distal portions 32. The base plate 12 illustrated in FIGS. 5 and 6, is intended to span two vertebral bodies. Although the base plate 12 is adapted to span two vertebral bodies, the base plate 12 may be designed to span anywhere from two to four vertebral bodies.

Each distal portion 32 may be attached to a different vertebra using fasteners, such as screws that pass through screw holes 16. Because the distal portions 32 are similar, only the operation of one distal portion is described in detail. Each screw hole 16 has a substantially circular shape and the inner portion of the screw hole 16 has substantially spherical curvatures. The ends of the distal portions 32 of the base plate are configured with a spherical curvature. The spherical curvature of the ends of base plate 12 are provided so as to correspond to the extension plate 14. As illustrated in FIGS. 1-4, the extension plate 14 is provided with a spherical curvature that corresponds to the base plate 12 so that the coupling of the base plate 12 and the extension plate 14 provide a fit that inhibits lateral motion.

The base plate 12 is also configured with at least one graft window 18 that is positioned between adjacent screw holes 16. In this embodiment, the base plate 12 illustrates two graft windows 18 positioned between the two distal ends of the base plate 12. Each of the graft windows 18 have edges and at least one of these edges are configured to be able to receive the hook element or any type of connection element associated with the extension plate. The connection element and the extension plate will be discussed in greater detail with reference to FIGS. 7 and 8.

The base plate 12 is shaped so that its bottom surface has a bi-concave curvature, being concave both in the longitudinal plane and in the transverse plane. The concave curvature in the longitudinal plane conforms to the proper shape of the anterior aspect of the spine with the vertebrae aligned in the appropriate lordosis. The base plate generally has a thickness between 2.0 mm to 4.0 mm, and a thickness of 2.3 mm is preferred.

The base plate 12 is also provided with a screw locking mechanism 24 that is positioned to be adjacent to each screw hole. The locking mechanism 24 is provided with a threaded set screw that when actuated, blocks the back out of the bone screw. Specifically, the locking mechanism inhibits the axial and rotational movement of the bone screws once the plate is affixed to the vertebral bodies. FIGS. 1-8 illustrate the locking mechanism 24 in which the set screw is permanently housed in an aperture adjacent to the screw holes. When the set screw is in an unlocked position, the bone screw can be positioned within the screw hole and advanced into the vertebrae. As the set screw is actuated by using a screw driving instrument, a portion of the set screw inhibits the bone screw from backing out of the vertebral body.

The plate system of the present invention may be configured to aid in the insertion of bone screws. For example, both the base plate and the extension plate may have one or more openings that are capable of securely receiving a drill guide. For example, the screw holes may be configured with treads that engage with a threaded tip of a drill guide. In addition, the plate may also have one or more recesses, pivot points, depth stops, or areas of removed material in the top surface of the plate that help align the drill guide opening over the holes of the plate. The drill guide may have a rotating barrel that rotates along an axis that extends through the recess of the plate.

Figure 7:
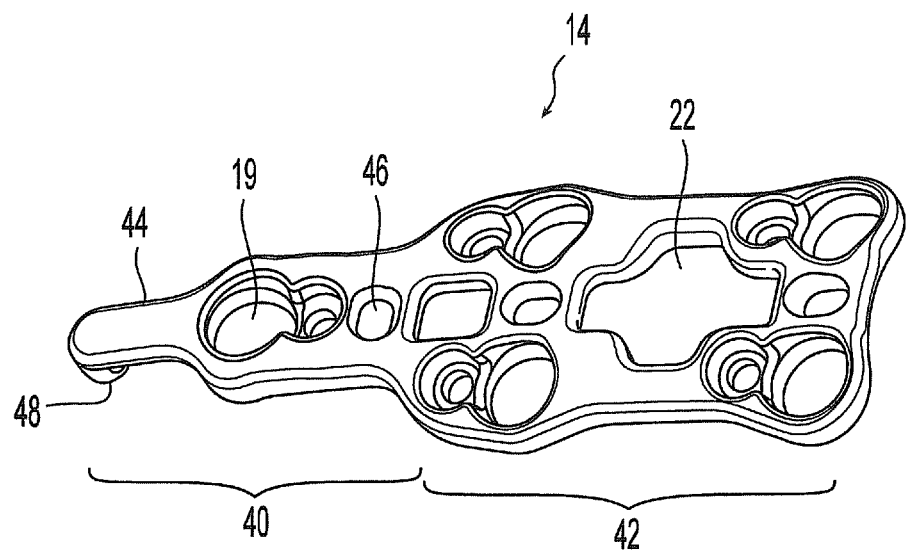
FIG. 7 is an isometric view of an extension plate according the present invention.

FIGS. 7 and 8 illustrate more clearly the extension plate according to the present invention. The extension plate 14 is configured with a proximal end 40 and a distal end 42. The proximal end 40 is configured to be narrower in width than the distal end 42 of the extension plate 14. The proximal end 40 is also provided with a finger portion 44 that is configured and dimensioned to connect with the base plate 12. The proximal end 40 of the extension plate 14 is provided with a screw hole 19 and a instrument guide hole 46 as well as a graft windows 22. The screw hole 19 is configured and dimensioned to receive a bone screw that is inserted into the vertebrae at an angle that positions the screw between the bone screws of the adjacent base plate.

Figure 8A:
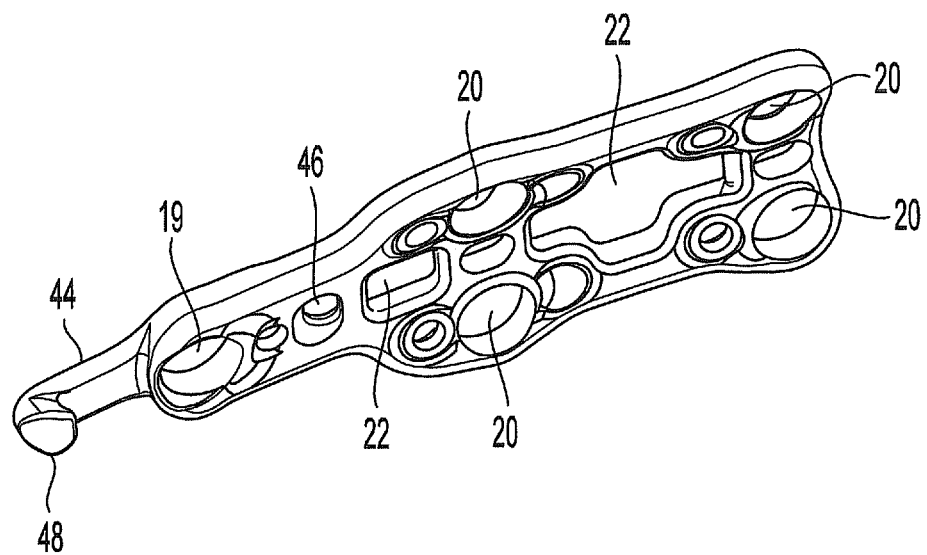
FIG. 8A is a bottom view of the extension plate according to the present invention.
Figure 8B:
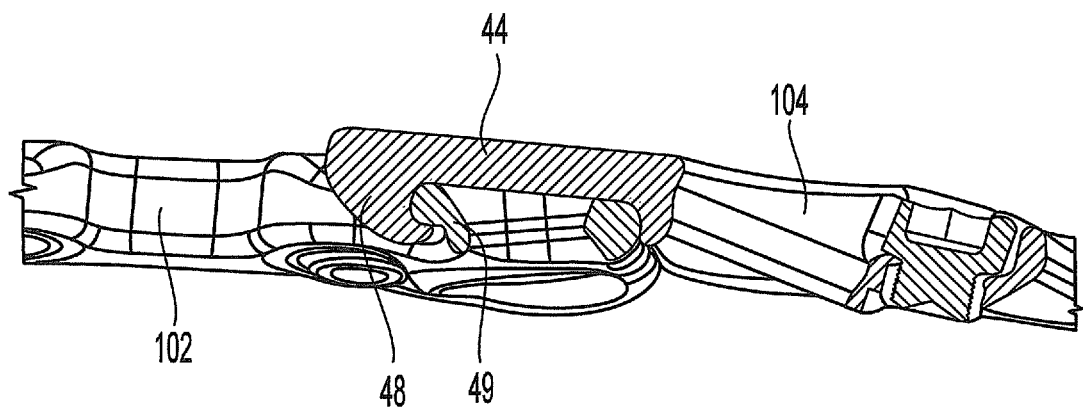
FIG. 8B is a cross-sectional view of the connection between the base plate and the extension plate.

In this particular embodiment, the finger portion 44 is further configured with a hook element 48 which is used to connect to the base plate 12. The hook element 48, as illustrated in FIGS. 7, 8A, and 8B, is configured to be able to couple with the graft window portion 22 of the base plate 12. FIG. 8b more clearly illustrates the connection between the base plate 102 and the extension plate 102. The hook element 48 is connected at the bottom edge 49 of the graft window 18 of the base plate 102. It should be noted that the thickness and dimensions of the hook element 48 and the finger portion 44 of the extension plate may be adjusted and configured to optimize the space available in the anterior portion of the spine. Although, the present embodiment illustrates a hook element, various other mechanisms such as clips, notches, dovetails and others may be used to connect one plate to another. Any type of connection element connecting the extension plate to the base plate may be used. Also illustrated in FIG. 8, the extension plate 14 is provided with a graft window 22 having an edge that is capable of receiving a hook element or any type of connection element from another extension plate.

Figure 9A:
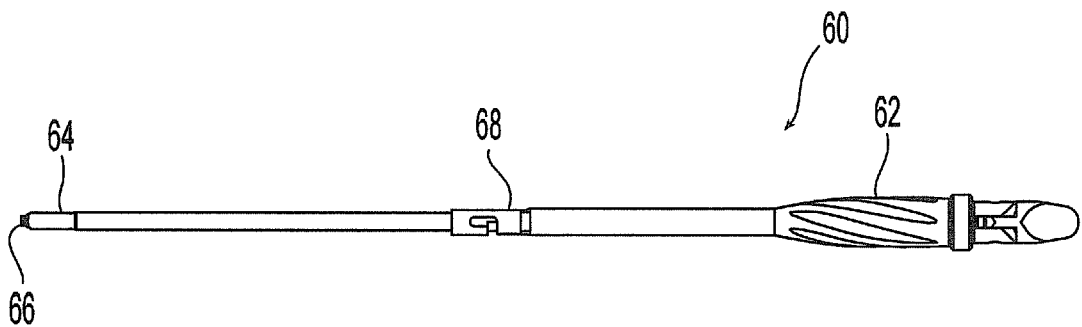
FIGS. 9A-9C illustrate a plate holding instrument in various views according the present invention.
Figure 9B:
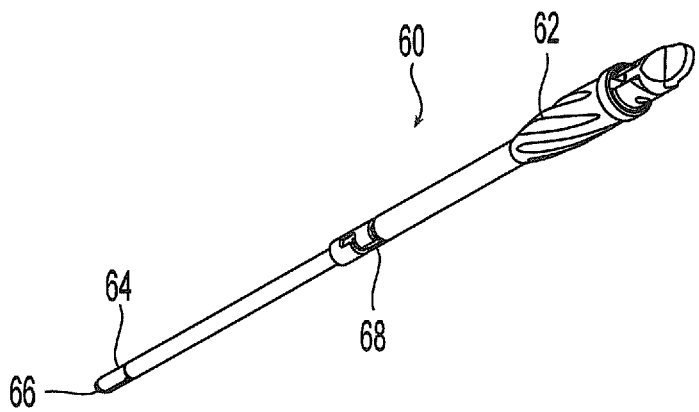
Figure 9C:
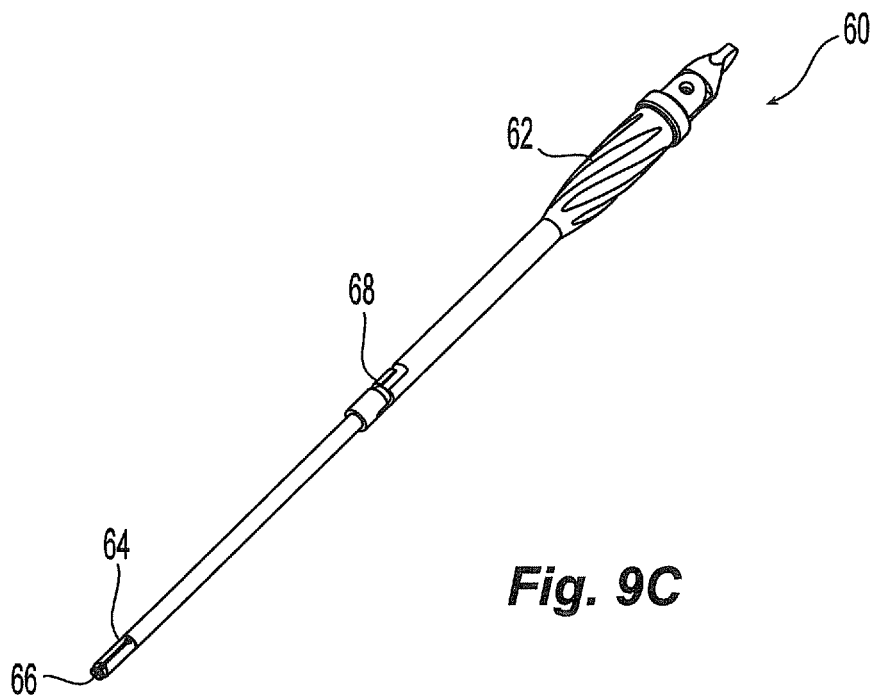

FIGS. 9A, 9B, and 9C illustrate an instrument 60 for implanting the base plate and the extension plate within the spine. The instrument 60 is configured with a proximal portion 62 and a distal portion 64. The distal portion 64 is configured with an end 66 that is coupled with the instrument 60 receiving hole 46 in the base plate and/or extension plate. The implanting instrument 60 also includes a middle portion 68 that contains a coupling element to receive a variable drill guide for directing a bone screw through the screw hole of the base plate and/or the extension plate.

Figure 10:
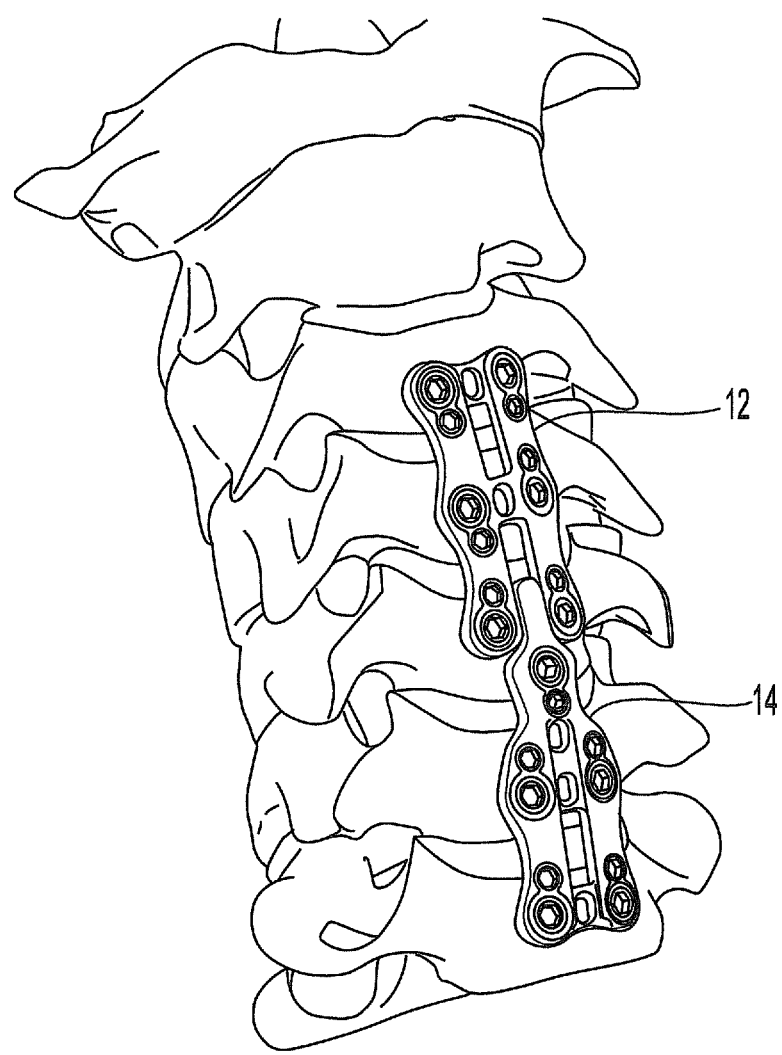
FIG. 10 illustrates the plate system according to present invention.

FIG. 10 illustrates the present invention positioned on the anterior portion of spine. The base plate 12 and the extension plate 14 are positioned over five levels of the spine.

Figure 11:
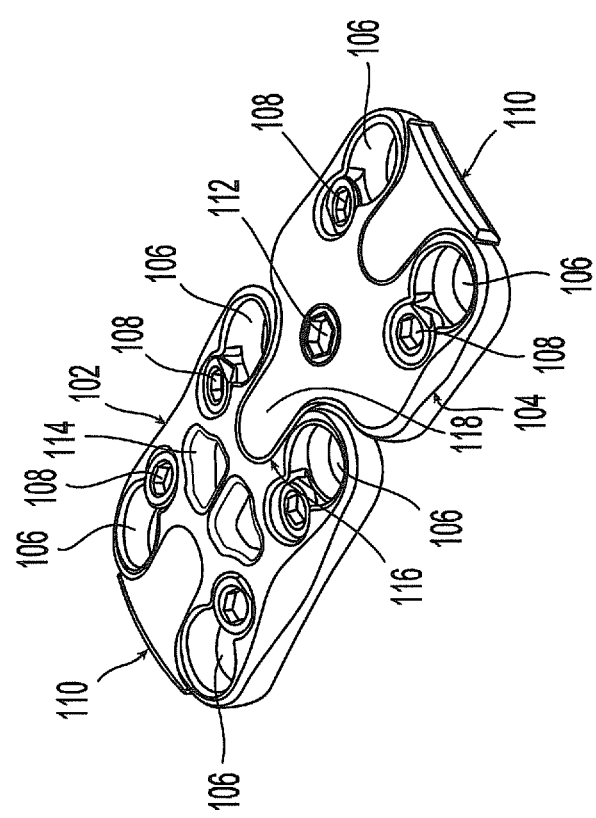
FIG. 11 is an isometric view of another embodiment of the present invention.
Figure 12:
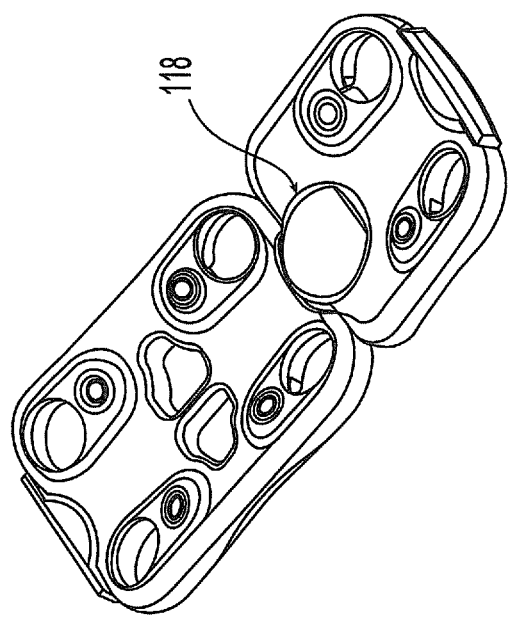
FIG. 12 is a bottom view of the embodiment illustrated in FIG. 11.
Figure 13E:
FIGS. 13A-13E are the top, bottom and side views of the base plate according to another embodiment of the present invention.
Figure 13A:
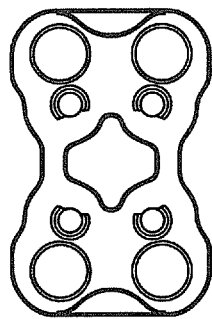
Figure 13B:
Figure 13C:
Figure 13D:
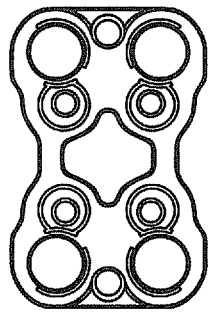
Figure 16:
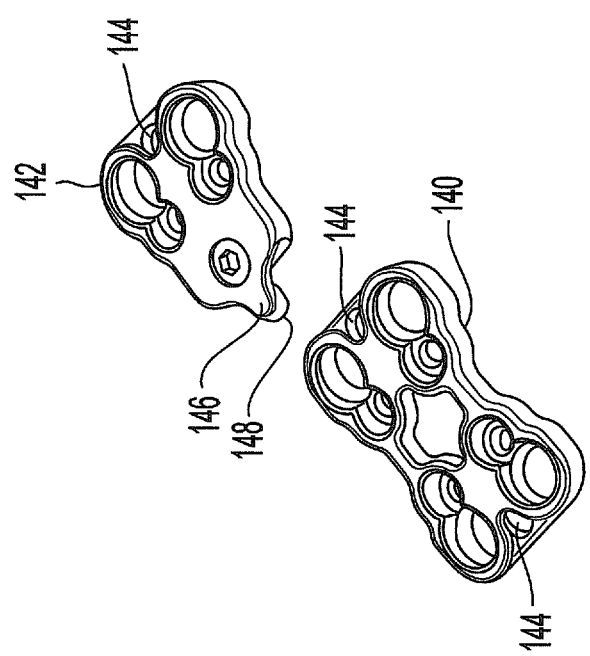
FIG. 16 is an isometric view of the base plate and the adjacent segment plate according the another embodiment of the present invention.
Figure 17A:
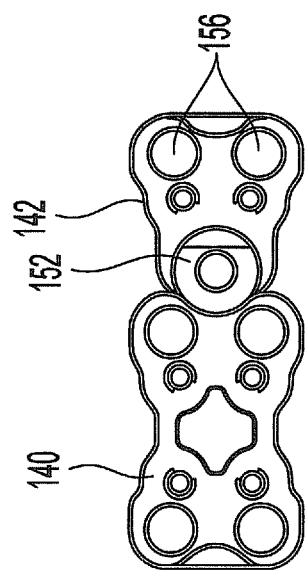
Figure 17C:
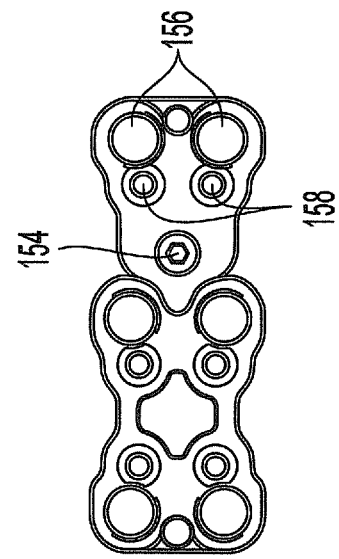

Now turning to FIGS. 11 and 12, another embodiment of the present invention is illustrated. In these particular embodiments, the anterior plating system 100 consists of a base plate 102 and an adjacent segment plate 104, if needed. It should be noted that the adjacent segment plate 104 is only used when the patient's diagnosis dictates it. The base plate 102 is provided with cavities on both ends so that if additional segment plates are required, they can be incorporated either superiorly or inferiorly depending on where the patient requires treatment. As can be seen in FIG. 11, the base plate 102 and the adjacent segment plate 104 are provided with features that allow for joining. The base plate 102 and adjacent segment plate 104 are geometrically shaped to provide bone screw holes 106, blocking set screws 108 and graft windows 114. The adjacent segment plate 104 is also provided with a sleeve for incorporating additional segment plates, if needed. A hexagonal drive screw 112 in combination with a fastener 118 is used to lock the adjacent segment plate 104 to the base plate 102. The base plate 102 and the adjacent segment plate 104 are both provided with end caps 110 which cover the cavity where a finger portion 118 from an adjacent segment plate 104 is received.

FIGS. 13-15 illustrate the components of the present system. Specifically, FIGS. 13A-13E illustrate the base plate according to the one embodiment of the present invention. FIGS. 13A-13E illustrate the top, bottom, and side views of the base plate 102. As can be seen in FIG. 13E, the base plate 102 is provided with a concave geometry to conform with the shape of the anterior spine.

FIGS. 14A-14E illustrate the top, bottom, and side views of an adjacent segment plate according to one embodiment of the present invention. The adjacent segment plate 122 is shown have a two screw holes 124 and screw blocking mechanisms 126. The adjacent segment plate is also shown having a finger portion 128 having a lip 130. The lip 130 is inserted into the cavity of the base plate. FIG. 14A also illustrates a hex screw drive 132 for actuating the fastener element 134. The fastener element 134 is actuated or turned when the screw drive 132 is operated with a hex screw driver to lock the adjacent segment plate to the base plate. FIGS. 15A-15E illustrate the different views of the fastening element. As seen in FIG. 15B, the fastener is operated as a cam device to lock the adjacent segment plate with the base plate. The fastener 134 is positioned within the cavity of the base plate when turned by the hex screw driver.

Now turning to FIGS. 16 and 17A-17C, the connection of the base plate 140 with the adjacent segment plate 142 will be described in greater detail. During surgery, the base plate 140 is readied for receiving the adjacent segment plate 142 by removing the end cap (not shown) positioned on either the superior or inferior portion of the base plate 140. After the end cap is removed and the cavity 144 is cleaned of any tissue, the finger portion 146 of the adjacent segment plate 142 is inserted into the receiving pocket cavity 144 of the base plate 140. At the tip of the finger portion 146, there is provided a curved lip 148 which is inserted into an accommodating lip reception area 150 (FIG. 19A) located in the cavity of the base plate 140.

The position of the adjacent segment plate can be adjusted since they provide space between the curvature of the finger portion and the curved outer portion of the screw hole. In one embodiment, the adjacent segment plate is adjustable 4 degrees from the medial axis of the spine. Once the desired alignment is made, the hex drive fastener 152 is rotated to the left until the alignment arrows meet and both plates are rigidly connected. The hex drive fastener 152 is a disc shaped device that utilizes the geometry of the plate to draw the plates together tightly. The adjacent segment plate is then attached to the vertebral body through the use of bone screws inserted in the screw holes 158. Once the bone screws are positioned, the blocking mechanisms 158 are actuated to inhibit the bone screws from backing from the vertebra and plate.

Figure 18C:
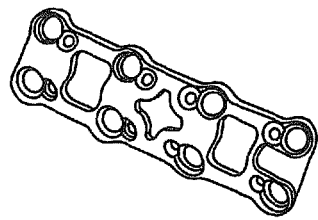
FIGS. 18-18E are the additional embodiments of the base plate and the adjacent segment plate according to the present invention.
Figure 18B:
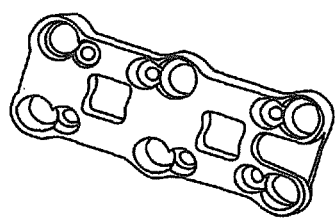
Figure 18E:
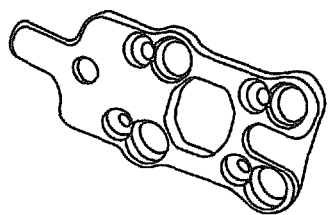
Figure 18A:
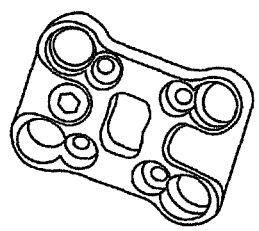
Figure 18D:
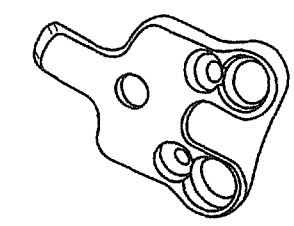

FIGS. 18A-18C illustrate a one, two, and three level base plate and FIGS. 18D and 18E illustrate a one and two level adjacent segment plate.

Figure 19:
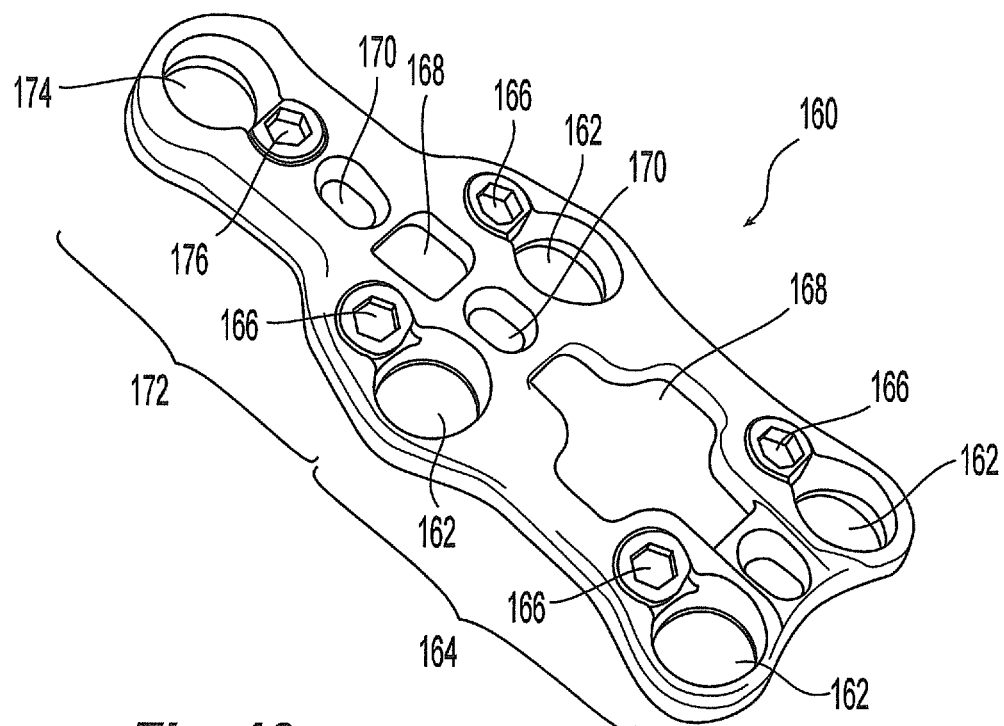
FIGS. 19 and 20 illustrate additional embodiments of the extension plate according to the present invention.
Figure 20:
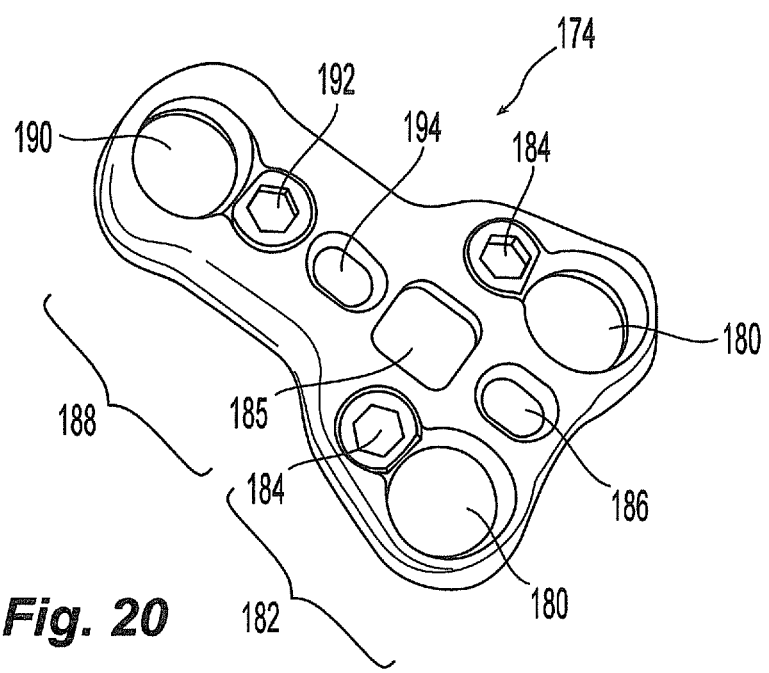

FIGS. 19 and 20 illustrate yet another embodiment of the extension plates according the present invention. FIG. 19 illustrates a two level extension plate 160 having a plurality of screw holes 162 in a base portion 164 with adjacent screw locking mechanisms 166. The base portion 164 is provided with multiple graft windows 168 and an instrument receiving hole 170. The extension portion of the extension plate is provided with a screw hole 174, screw locking mechanism 176, and an instrument receiving hole 170. The extension portion 170 is configured to be narrower than the base portion 164 of the extension plate 160. The screw hole 170 is capable receiving bone screws that are directed to be inserted into the vertebra. In this embodiment of the present invention, the screw hole 174 is configured to angulate so that the bone screw is directed at an angle in which the bone screw is situated between the bone screws that have already been inserted into the vertebrae for implanting a base plate.

FIG. 20 illustrates a one level extension plate 178 having a plurality of screw holes 180 in a base portion 182 with adjacent screw locking mechanisms 184. The base portion 182 is provided with a graft windows 185 and an instrument receiving hole 186. The extension portion 188 of the extension plate is provided with a screw hole 190, a screw locking mechanism 192, and an instrument receiving hole 194. The extension portion 188 is configured to be narrower than the base portion 182 of the extension plate 178. The screw hole 190 is capable receiving bone screws that are directed to be inserted within the vertebra while stabilizing and coupling the extension plate 178 to the vertebrae. In this embodiment of the present invention, the screw hole 190 is configured to angulate so that the bone screw is directed at an angle in which the bone screw is situated between the bone screws that have already been inserted into the vertebrae for implanting a base plate.

Although the present invention and its advantages have been described in detail, it should be understood that various changes, substitutions, and alterations can be made herein without departing form the spirit and scope of the invention as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A spine stabilization system comprising:
a base plate having a plurality of screw holes and a plurality of corresponding screw locking mechanisms, wherein the base plate screw holes extend from atop surface of the base plate to a bottom surface of the base plate;
an extension plate having a plurality of screw holes and corresponding screw locking mechanisms, wherein the extension plate screw holes extend from a top surface of the extension plate to a bottom surface of the extension plate,
wherein the extension plate is dimensioned and configured with an extension portion, the extension portion having a screw hole and a screw locking mechanism and a finger portion having a connection element to couple with the base plate, wherein the finger portion comprises a hook element having downwardly curved surface that creates a recess for the base plate, wherein an upper surface of the hook element is in contact with a lower surface of the base plate when the base plate is received in the recess of the hook element,
wherein the base plate is provided with graft windows having edges, wherein one of the edges is configured to receive and couple with the connection element,
wherein the extension plate is positioned over the base plate such that a bottom surface of the extension plate is in contact with a top surface of the base plate when the extension plate is joined to the base plate.

2. The spine stabilization system of claim 1, wherein the extension plate comprises at least four screw holes for receiving bone screws therein.

3. The spine stabilization system of claim 2, wherein the base plate and the extension plate includes curved sidewalls.

4. The spine stabilization system of claim 1, wherein the connection element is a clip.

5. The spine stabilization system of claim 3, wherein the base plate has a first end and a second end, wherein the first end and the second end are curved.

6. The spine stabilization system of claim 5, wherein the graft windows of the base plate have lengths greater than adjacent base plate screw holes.

7. The spine stabilization system of claim 6, wherein at least one of the graft windows of the base plate is positioned on a midline of the plate, while at least one of the base plate screw holes is offset from a midline of the plate.

8. The spine stabilization system of claim 1, wherein the screw hole in the extension portion is configured to direct a bone screw to be positioned between bone screws positioned through a bottom portion of the base plate.

9. A spine stabilization system comprising:
a base plate having a plurality of screw holes and a plurality of corresponding screw locking mechanisms, wherein the base plate screw holes extend from a top surface of the base plate to a bottom surface of the base plate;
an extension plate having a plurality of screw holes, wherein the extension plate screw holes extend from a top surface of the extension plate to a bottom surface of the extension plate,
a plurality of bone screws,
wherein the extension plate is dimensioned and configured with an extension portion, the extension portion having a screw hole and a screw locking mechanism and a finger portion having a connection element to couple with the base plate, wherein the finger portion comprises a hook element having a downwardly curved surface that creates a recess for the base plate, wherein an upper surface of the hook element is in contact with a lower surface of the base plate when the base plate is received in the recess of the hook element,
wherein the base plate is provided with graft windows having edges, and wherein at least one of the edges is configured to receive and couple with the connection element,
wherein at least one of the plurality of bone screws is positioned within one of the plurality of screw holes in the extension plate,
wherein the extension plate is positioned over the base plate such that a bottom surface of the extension plate is in contact with a top surface of the base plate when the extension plate is joined to the base plate.

10. The spine stabilization system of claim 9, wherein the extension plate comprises at least four screw holes for receiving bone screws therein.

11. The spine stabilization system of claim 10, wherein the base plate and the extension plate includes curved sidewall.

12. The spine stabilization system of claim 9, wherein the connection element is a clip.

13. The spine stabilization system of claim 9, wherein the base plate has a first end and a second end, wherein the first end and the second end are curved.

14. The spine stabilization system of claim 13, wherein the first and second end have spherical curvatures.

15. The spine stabilization system of claim 13 wherein at least one of the graft windows of the base plate is positioned on a midline of the plate, while at least one of the base plate screw holes is offset from a midline of the plate.

16. The spine stabilization system of claim 9, wherein the screw hole in the extension portion is configured to direct a bone screw to be positioned between bone screws positioned through a bottom portion of the base plate.

17. An extension plate system for stabilizing a spine comprising:
a base plate; and
an extension plate comprising:
a base portion having a plurality of screw holes and corresponding screw locking mechanisms, wherein the base portion screw holes extend from a top surface of the base portion to a bottom surface of the base portion;
an extension portion, the extension portion having an angled screw hole and a screw locking mechanism, wherein the extension portion comprises screw holes that extend from a top surface of the extension portion to a bottom surface of the extension portion; and
a finger portion, the finger portion configured with a connection element to contact and connect with the base plate, wherein the finger portion comprises a hook element having a downwardly curved surface that creates a recess for the base plate,
wherein an upper surface of the hook element is in contact with a lower surface of the base plate when the base plate is received in the recess of the hook element,
wherein the extension portion is positioned over the base plate such that a bottom surface of the extension portion is in contact with a top surface of the base plate when the extension plate is joined to the base portion.

18. The extension plate system of claim 17, wherein the base portion includes at least four screw holes and a graft window positioned therebetween.

19. The extension plate system of claim 17, wherein the base plate includes a graft window, and wherein the extension portion is in contact with a lower edge of the graft window when the base plate is joined with the extension portion, and wherein at least a portion of the graft window remains exposed even when the base plate is joined with the extension portion.

* * * * *